(12) United States Patent
Krishnan et al.

(10) Patent No.: US 6,582,429 B2
(45) Date of Patent: Jun. 24, 2003

(54) ABLATION CATHETER WITH COVERED ELECTRODES ALLOWING ELECTRICAL CONDUCTION THERETHROUGH

(75) Inventors: Mohan Krishnan, Shoreview, MN (US); Wade A. Bowe, Temecula, CA (US); David S. Wood, Temecula, CA (US); Jeffrey A. Hall, Birmingham, AL (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/902,038

(22) Filed: Jul. 10, 2001

(65) Prior Publication Data

US 2003/0014044 A1 Jan. 16, 2003

(51) Int. Cl.⁷ .............................................. A61B 18/18
(52) U.S. Cl. ........................................ 606/41; 600/372
(58) Field of Search ........................ 606/41, 32, 34, 606/45, 47, 48, 50, 372; 600/381, 373, 374

(56) References Cited

U.S. PATENT DOCUMENTS

| | | | | |
|---|---|---|---|---|
| 5,520,684 A | * | 5/1996 | Imran | 606/41 |
| 5,938,597 A | * | 8/1999 | Stratbucker | 600/382 |
| 6,042,959 A | * | 3/2000 | Debe et al. | 204/283 |
| 6,078,830 A | * | 6/2000 | Levin et al. | 600/374 |
| 6,097,976 A | * | 8/2000 | Yang et al. | 600/373 |
| 6,208,881 B1 | * | 3/2001 | Champeau | 600/374 |
| 6,256,525 B1 | * | 7/2001 | Yang et al. | 600/373 |
| 6,327,487 B1 | * | 12/2001 | Stratbucker | 600/382 |
| 6,400,976 B1 | * | 6/2002 | Champeau | 600/374 |
| 6,413,255 B1 | * | 7/2002 | Stern | 606/41 |

* cited by examiner

*Primary Examiner*—Michael Peffley
*Assistant Examiner*—Peter Vrettakos
(74) *Attorney, Agent, or Firm*—Fulwider Patton Lee & Utecht, LLP (57) ABSTRACT

A surface covering including a primary layer of a porous polymer structure and a secondary surface covering one or both of a metallic element layer and a hydrophilic layer is positioned over the surface of an ablation electrode. The pores of the surface covering are sized such that blood platelets are prevented from contacting the surface of the electrode while physiological fluid is allowed to pass through and contact the electrode surface to hereby provide a conduction path for current from the electrodes. The surface covering may further include an electrically non-conductive and thermally conductive portion positioned over another portion of the electrode to prevent alternate or non-intended site ablations.

28 Claims, 6 Drawing Sheets

ABLATION CATHETER WITH COVERED ELECTRODES ALLOWING ELECTRICAL CONDUCTION THERETHROUGH

BACKGROUND OF THE INVENTION

1. Field of the Invention

The invention relates generally to an electrophysiological ("EP") catheter for providing energy to biological tissue within a biological site, and more particularly, to an EP catheter having a surface covering over its electrodes that prevents adhesion of coagulum forming blood platelets to the electrode surface while still allowing electrical conduction therethrough.

2. Description of the Related Art

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system providing RF ablation therapy. In this therapy, transmural ablation lesions are formed in the atria to prevent atrial reentry and to allow sinus impulses to activate the entire myocardium.

During ablation, electrodes carried by an EP catheter are placed in intimate contact with the target endocardial tissue. RF energy is applied to the electrodes to raise the temperature of the target tissue to a non-viable state. In general, the temperature boundary between viable and non-viable tissue is approximately 48° Celsius. Tissue heated to a temperature above 48° C. becomes non-viable and defines the ablation volume. The objective is to elevate the tissue temperature, which is generally at 37° C., fairly uniformly to an ablation temperature above 48° C., while keeping both the temperature at the tissue surface and the temperature of the electrode below 100° C. When the blood temperature reaches approximately 100° C., coagulum generally occurs.

Blood coagulation is a major limitation/complication associated with RF ablation therapy. Coagulation can lead to thromboembolism and can also form an insulating layer around the electrode hindering further energy delivery required for ablation therapy. Heat appears to be a major factor in the formation of blood coagulum on a catheter electrode. During a typical RF energy ablation procedure using an EP catheter, on or more electrodes carried by the catheter are positioned such that a portion of the electrodes are in contact with the tissue being ablated while the remaining portion of the electrodes are in contact with blood. The RF energy applied during the procedure resistively heats the tissue which in turn heats the electrode through conduction. As blood stays in contact with the heated electrode, platelet activation occurs. This platelet activation appears to lead to coagulum formation.

Hence, those skilled in the art have recognized a need for providing a catheter with ablation electrodes that reduce or inhibit the formation of coagulum by preventing platelets and other substances from adhering to the electrode surface all without adversely affecting the electrical conductivity of the ablation electrode. The invention fulfills these needs and others.

SUMMARY OF THE INVENTION

Briefly, and in general terms, the invention is directed to an ablation catheter having a surface covering over its electrodes that prevents adhesion of blood platelets to the electrode surface while still allowing electrical conduction therethrough.

In a first aspect, the invention relates to a catheter for applying energy to biological tissue having biological fluid flowing thereby. The catheter includes a shaft having at least one electrode and a layer of a bio-compatible, non-electrically conductive porous structure covering at least a portion of the surface of the electrode. By incorporating a bio-compatible, non-electrically conductive porous structure coating or covering over the ablation electrode adhesion of blood platelets on the electrode surface is prevented or at least substantially minimized. As such, coagulum causing components of the blood cannot contact the electrode and coagulation cannot begin and therefore, not propagate.

In a detailed facet of the invention the bio-compatible, non-electrically conductive porous structure is a polymer structure and may include either one of a porous homopolymer or a porous copolymer. In a further detailed aspect, the porous homopolymer and the porous copolymer is based on anyone of polyurethanes, polyesters, polyolefins, polyamides, ionomers and fluoropolymers. In another detailed facet, the catheter further includes a layer of a metallic element covering the interiorwalls of the pores of the bio-compatible, non-electrically conductive porous structure. In yet another detailed aspect the catheter further includes a layer of a wetting agent covering the metallic element. In the absence of the metallic element, the interior walls of the bio-compatible, non-electrically conductive porous structure may be covered with a secondary surface such as a hydrophilic material or a plasma modified material. In another detailed aspect of the invention, the electrode includes a first surface portion and a second surface portion;

the shaft is adapted to position the electrode adjacent the biological tissue such that the first surface portion contacts the tissue and the second surface portion remains in the fluid; and the layer of a bio-compatible, non-electrically conductive porous structure covers the first surface portion. In a further detailed aspect the catheter further comprises a layer of bio-compatible, non-electrically conductive structure covering the second surface portion.

In another aspect, the invention relates to a catheter for applying energy to biological tissue having biological fluid flowing thereby. The catheter includes a shaft having a curved distal-end region with an inner surface and an outer surface and a plurality of band electrodes positioned at the distal-end region of the shaft. The catheter further includes a surface covering including a first portion comprising a bio-compatible, non-electrically conductive porous structure covering a portion of each of the band electrodes.

In a detailed aspect of the invention, the surface covering further covers a portion of the shaft between band electrodes. In another detailed facet, each of the band electrodes includes a first surface portion that lies on the outer surface and a second surface portion that lies on the inner surface. The shaft is adapted to position the outer surface adjacent the biological tissue and the inner surface in the fluid. The first portion of the surface covering covers the first surface portion of each band electrode. In a further detailed aspect, the surface covering further includes a second portion comprising a bio-compatible, non-electrically conductive non-porous structure that covers the second surface portion of each band electrode. In further detailed aspects, the bio-compatible, non-electrically conductive structure comprises a porous polymer structure while the bio-compatible, non-electrically conductive structure comprises a non-porous polymer structure.

In another aspect, the invention relates to a catheter for applying energy to biological tissue having biological fluid flowing thereby that includes a shaft having a distal-end region carrying a plurality of band electrodes. The distal-end region defines a tissue-contacting surface and a fluid-contacting surface. A surface covering including a first portion comprising a bio-compatible, non-electrically conductive porous structure covers the portion of each of the band electrodes coincident with the tissue-contacting surface. In a detailed facet of the invention, the surface covering also includes a second portion comprising a bio-compatible, non-electrically conductive non-porous structure that covers the portion of each of the band electrodes coincident with the fluid-contacting surface.

These and other aspects and advantages of the invention will become apparent from the following detailed description and the accompanying drawings which illustrate by way of example the features of the invention.

DETAILED DESCRIPTION OF THE PREFERRED EMBODIMENTS

Figure 1:
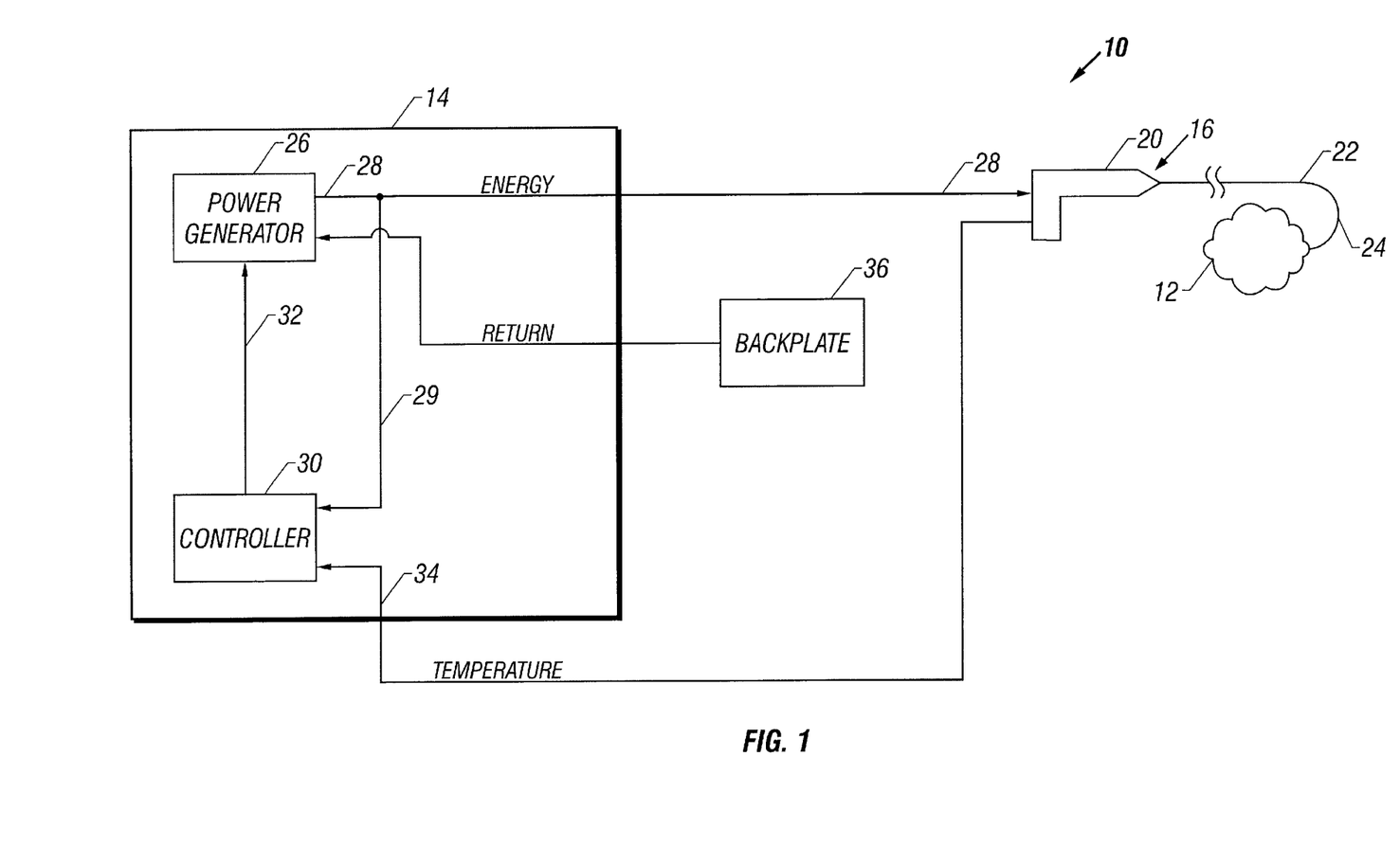
FIG. 1 is a schematic block diagram of an ablation system including a power control system ("PCS") and a catheter system configured in accordance with aspects of the invention.

Turning now to the drawings, in which like reference numerals are used to designate like or corresponding elements among the several figures, in FIG. 1 there is shown a system 10 for use in ablation therapy of a biological site 12, e.g., the atrium or ventricle of the heart. The system 10 includes a power control system 14 and a catheter system 16. The catheter system 16 includes a handle 20 and a steerable catheter sheath 22 having a distal segment 24. The distal segment 24 carries an electrode system (not shown) and is capable of being percutaneously introduced into a biological site.

The power control system 14 includes a power generator 26, that may have any number of output channels through which it provides power or drive 28 to the catheter system 16. The operation of the power generator 26 is controlled by a controller 30 which outputs control signals 32 to the power generator 26. The controller 30 monitors the power 28 provided by the power generator 26 along a power monitor line 29. In addition, the controller 30 also receives temperature signals 34 from the catheter system 16. Based on the power 28, and the temperature signals 34 the controller 30 adjusts the operation of the power generator 26.

The system 10 may further include a backplate 36. The backplate 36 is connected to the power generator 26 and generally provides a return path for the power 28 delivered to the biological site 12 through the catheter system 16.

Figures 2, 3:
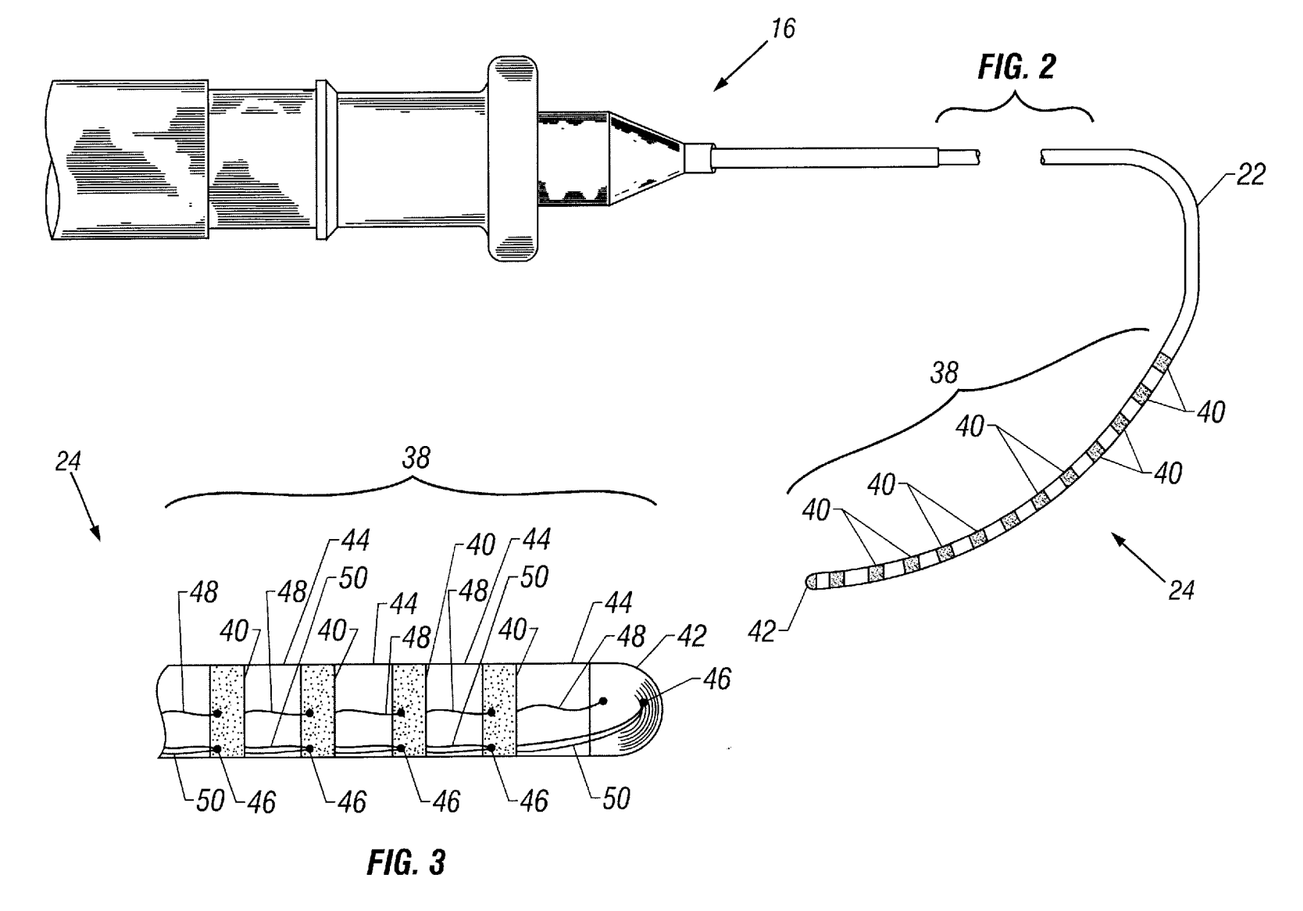
FIG. 2 is a diagram of the catheter system of FIG. 1 presenting more detail including a handle and a catheter sheath having a preformed distal segment carrying a linear array of electrodes having a surface covering.
FIG. 3 is a detailed schematic block diagram of a portion of the distal segment of the catheter system of FIG. 2, depicting a tip electrode and several band electrodes.

As shown in FIGS. 2 and 3, the distal segment 24 of the catheter system 16 includes an electrode system 38. The electrode system 38 is shown in schematic form with the components drawn in more detail to more clearly illustrate the relationship between the components. A preferred embodiment of the electrode system 38 includes twelve band electrodes 40 arranged in a substantially linear array along the distal segment 24 of the catheter sheath 22. The electrode system 38 may include a tip electrode 42. (For clarity of illustration, only four band electrodes 40 are shown in FIG. 3 although as stated, a preferred embodiment may include many more.) The band electrodes 40 are arranged so that there is space 44 between adjacent electrodes. In one configuration of the electrode system 38, the width of the band electrodes 40 is 3 mm and the space 44 between the electrodes is 4 mm. The total length of the electrode system 38, as such, is approximately 8 cm.

The arrangement of the band electrodes 40 is not limited to a linear array and may take the form of other patterns. A substantially linear array is preferred for certain therapeutic procedures, such as treatment of atrial fibrillation, in which linear lesions of typically 4 to 8 cm in length are desired. A linear array is more easily carried by the catheter sheath 22 and also lessens the size of the catheter.

The band electrodes 40 and tip electrode 42 are formed of a material having a significantly higher thermal conductivity than that of the biological tissue to be ablated. Possible materials include silver, gold, chromium, aluminum, molybdenum, tungsten, nickel, platinum, and platinum/10% iridium. Because of the difference in thermal conductivity between the electrodes 40, 42 and the tissue, the electrodes cool off more rapidly in the flowing fluids at the biological site. The band electrodes 40 are sized so that the surface area available for contact with fluid in the heart, e.g., blood, is sufficient to allow for efficient heat dissipation from the electrodes to the surrounding blood. In a preferred embodiment, the electrodes 40 are 7 French (2.3 mm in diameter) with a length of 3 mm and a thickness in the range of about 0.002 mm to about 0.010 mm.

Figure 4A:
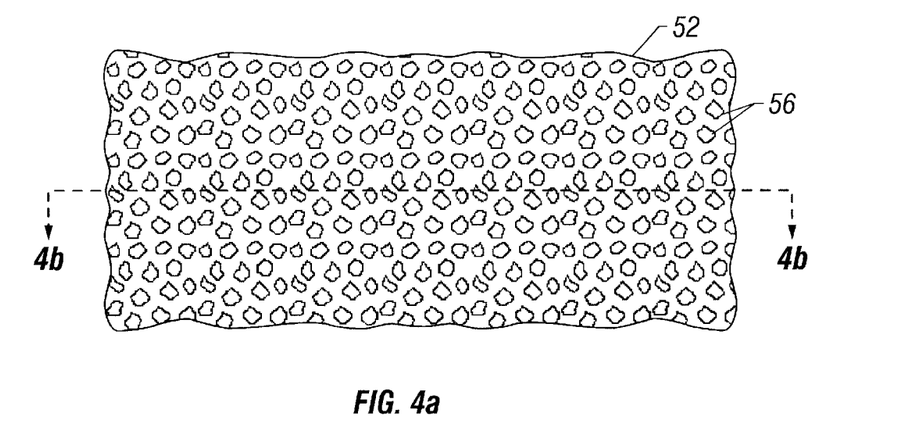
FIG. 4a is a plan view of the surface covering over an electrode.

Associated with the electrode system 38 are thermal sensors 46 for monitoring the temperature of the electrode system 38 at various points along its length. In one embodiment, each electrode 40, 42 has a thermal sensor 46 mounted to it. Each thermal sensor 46 provides a temperature signal 34 (FIG. 1) to the controller 30 which is indicative of the temperature of the respective band electrode 40 (FIGS. 2 and 3) at that sensor. In another embodiment of the electrode system 38 a thermal sensor 46 is mounted on every other band electrode 40. Thus for a catheter having twelve electrodes, there are thermal sensors on six electrodes. In yet another embodiment of the electrode system 38 the odd numbered electrodes have one thermal sensor 46 while the even numbered electrodes have two thermal sensors. In FIG. 3, which shows an embodiment having one thermal sensor for each electrode, there is shown a single power lead 48 for each electrode 40 to provide power to each electrode for ablation purposes and two temperature leads 50 for each thermal sensor 46 to establish a thermocouple effect. In alternate embodiments, the thermal sensors 46 may include thermistors, RTDs and fluoroptic probes With reference to FIGS. 4a through 4c, in accordance with the invention one or more of the electrodes 40,42 are covered or coated with any one of a variety of biocompatible, non-electrically conductive porous surface coverings 52. In one embodiment the surface covering 52 is a thin layer of porous homopolymer or copolymer structure 54 that is based on any one of polyurethanes, polyesters, polyolefins, polyamides, ionomers and fluoropolymers. In other embodiments the surface covering 52 may be a ceramic structure.

The layer is the polymer embodiment is no greater than about 100 microns thick. In a preferred embodiment, the polymer structure 54 comprises expanded polytetrafluoroethylene (ePTFE) which is obtained by mechanically drawing and orienting PTFE to make it porous using procedures well known to those skilled in the art. The ePTFE is drawn such that the average pore 56 size is less than 10 microns in diameter and is applied to the electrode surface using a sintering process at temperatures above 300° C. The ePTFE is also drawn such that the number of the pores per surface area, i.e., pore density, is large enough to allow sufficient electrical conduction for effective ablation using an acceptable level of energy. The pore density may be determined through experimental comparison of pore density, ablation lesion quality, e.g., size and depth, and energy level. Although depicted two dimensionally in FIG. 4b, the pores 56 throughout the polymer structure 54 form a three dimensional network of paths, much like those through a sponge.

Figure 4B:
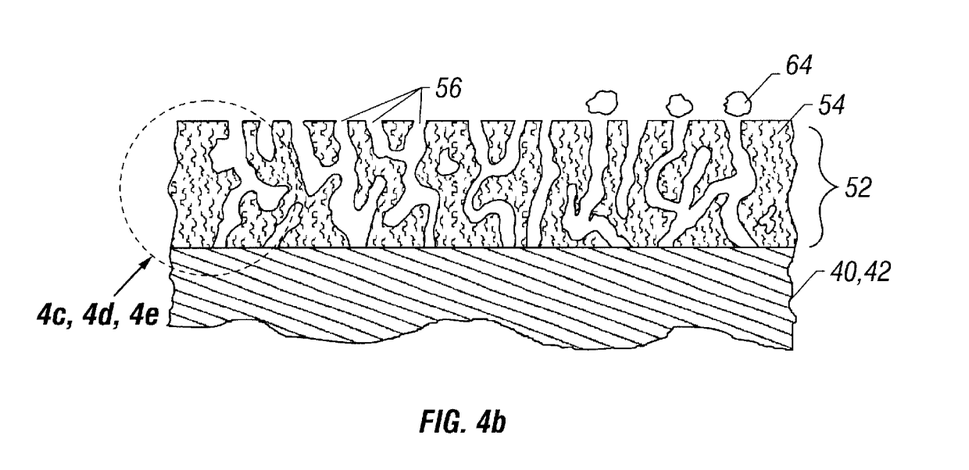
FIG. 4b is a cross section view of FIG. 4a along line 4b—4b depicting details of the surface covering over the electrode.
Figure 4C:
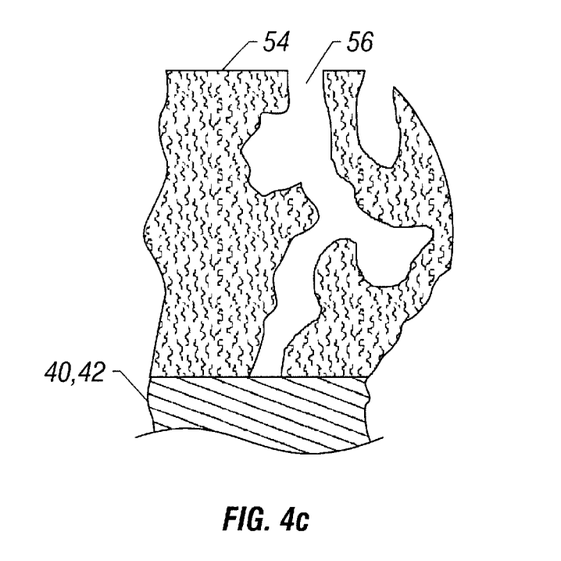
FIGS. 4c–4e are detail view of a portion of the surface covering of FIG. 4b depicting various configurations of the covering.

As shown in FIG. 4b, the pores 56 of the polymer structure 54 are, on one hand, too small to allow for platelets 64 to pass. As such they keep the coagulating substrates off the electrode 40, 42 surface. One the other hand, the pores 56 are large enough to allow electrically conductive fluids present within blood to pass through to the surface of the electrode 40, 42. The fluid fills the pores 56 and contacts the surface of the electrode 40, 42. Ablation energy is thus conducted from the electrode 40, 42 through the fluid, to the tissue (not shown) adjacent the surface of the porous polymer substrate 54.

Figure 4D:
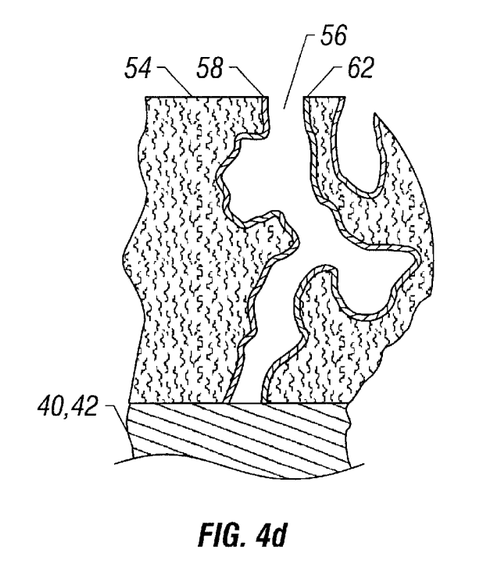
Figure 4E:
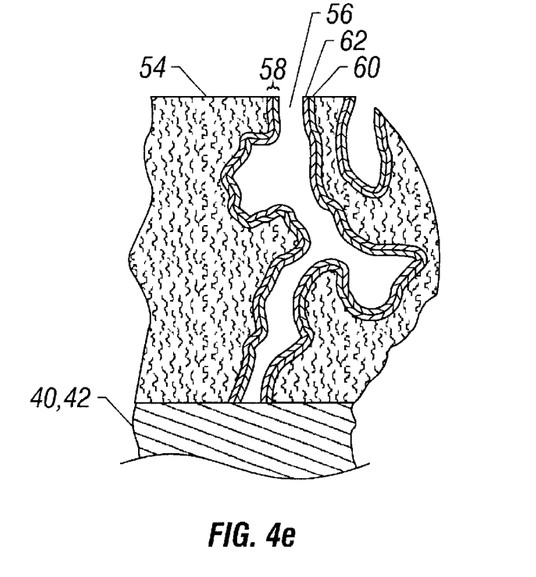

With reference to FIGS. 4d and 4e, in a preferred embodiment, the interior walls of the pores 56 of the porous polymer structure 54 are modified with a secondary surface 58. The secondary surface 58 does not completely cover the surface of the electrode 40, 42, thus a continuous path to the underlying electrode surface is maintained. In one embodiment (FIG. 4d) the secondary surface 58 is a layer of a wetting agent at most several microns thick. The wetting agent 62 comprises a hydrophilic material such as polyethylene oxide, polyethylene glycol, polyvinyl alcohol, polyvinyl pyrrolidone, gelatin, polymethacrylic acid, polyhydroxyethylmethacrylate, polyacrylamide and ionic and non-ionic surfacants based on fatty acid esters. The wetting agent 62 may be permanently attached to the interior walls of the pores of the porous polymer structure 54 using a chemical reaction process or it may be applied such that it dissolves into physiological fluid, e.g., the blood. The wetting agent 62 enhances the initial permeation of fluid through the pores 56 of the polymer structure 54 which may be hydrophobic. In another embodiment, the secondary surface 58 is a plasma modified or plasma polymerized layer, that makes the polymer readily wettable.

In another embodiment (FIG. 4e), the secondary surface includes a layer 60 of a metallic element, such as platinum, palladium, silver or gold. The metallic element may be a metallic alloy such as platinum-10% iridium. The metallic layer 60 is applied using any of the known methods of deposition of metals, such as an electroless process or a vapor deposition process. The metallic layer 60 is at most several microns thick and provides an electrical path from the electrode 40,42 surface to the tissue (not shown) adjacent the surface of the porous polymer structure 54. The metallic layer 60 electrical path complements the electrical path provided by the fluid and thus enhances the current distribution properties of the electrode 40, 42. While the top portion of the metallic layer 60 near the top surface of the polymer structure 54 is in contact with the blood, the thickness of the layer is selected such that electrical conductivity through the polymer structure 54 is enhanced without increasing the risk of coagulum formation. The thickness of the metallic layer 60 may be selected through experimental comparisons of conductivity level verses amount of coagulum formation for various layer thicknesses.

With continued reference to FIG. 4e, the secondary surface 58 may further include a layer of a wetting agent 62 applied over the metallic layer 60. The wetting agent 62 may be permanently attached to the metallic layer 60 using a chemical reaction process or it may be applied such that it dissolves into physiological fluid, e.g., the blood. Again, the wetting agent 62 enhances the initial permeation of fluid through the pores 56 of the polymer structure 54.

In another embodiment (not shown), the material of the metallic layer 60 and the material of the wetting agent 62 may be interspersed amongst one another to form a single layer. Additional embodiments of the secondary surface 58 may include a single layer of a metallic element 60.

The surface covering 52 may be applied to the electrodes 40, 42 prior to assembly of the catheter or after assembly of the catheter. If application takes place prior to assembly a masking may be applied to the area where no coating is desired (such as the inside diameter of the band electrode). Masking techniques are well known to those skilled in the art, accordingly details of such techniques are not provided. For ablation electrodes, non-coated areas are desired where wire attachment occurs. Alternately, electrode sub-assemblies with wire attachments can be covered with the surface covering 52 and then be used in subsequent catheter assembly processes.

Figure 5:
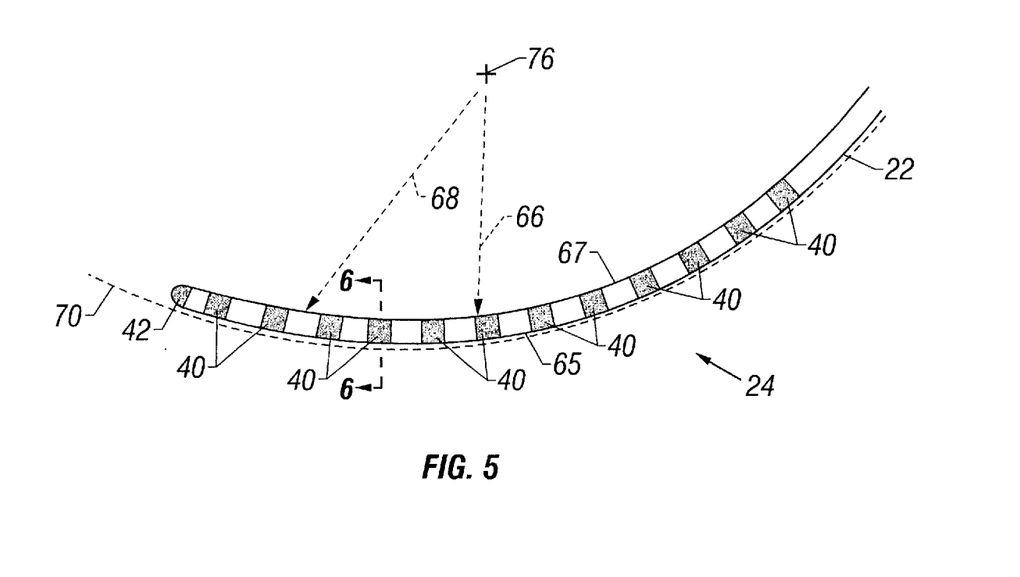
FIG. 5 is a diagram of the distal segment of the catheter system of FIG. 2 showing the inside and outside radii of curvature.

If application of the surface covering 52 takes place after assembly of the catheter, the covering may be applied only to the electrode 40, 42 by masking the sheath 22. Alternatively, the surface covering may also be applied to the entire distal end region of the catheter including the electrodes 40, 42 and the catheter sheath 22 (FIG. 5). When applied in this manner the surface covering 52 forms an outer polymer sleeve over the distal end region 24.

Figure 6:
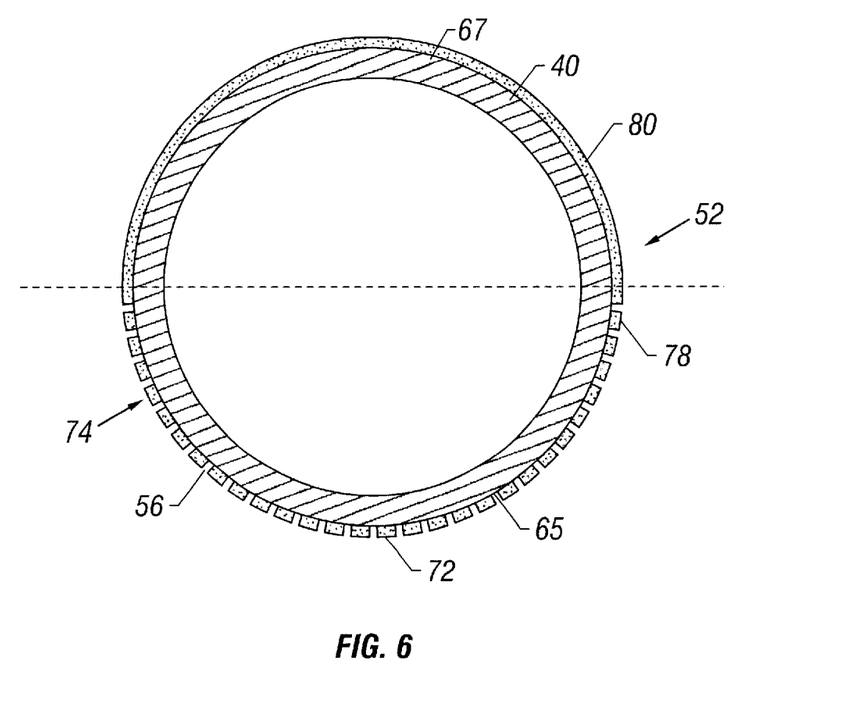
FIG. 6 is a cross-sectional view of one of the band electrodes of FIG. 5 along line 6—6, depicting a surface covering around a band electrode.

As shown in FIGS. 5 and 6, the distal region 24 of a deflected catheter shaft 22 has an outer surface 65 having an outside radius of curvature 66 and an inner surface 67 having an inside radius of curvature 68 both of which are referenced to the point identified by numeral 76. The outside radius of curvature 66 is defined by the longitudinal line 70 positioned at the outer most point 72 of the outer half 74 of the catheter, most distant from a reference center point 76 of the distal end region 24 curve. In FIG. 5, the longitudinal line 70 is shown slightly removed from the catheter shaft 22 for clarity of illustration in order to more clearly identify the outside radius of curvature. During ablation procedures, it is intended that the outer surface 65 contact the biological tissue undergoing ablation and that the inner surface 67 be in the blood pool.

Although FIG. 6 is a cross-sectional view at a location referenced to FIG. 5, it also presents another embodiment of the invention in which the surface covering 52 includes a porous polymer portion 78 and a nonporous polymer portion 80. The porous polymer portion 78 is similar to that shown and described with reference to FIGS. 4a through 4e. A simplified depiction of the porous polymer portion 78 is shown in FIG. 6 in order to clearly distinguish between the porous polymer portion and the nonporous polymer portion 80 of the surface covering. The thickness of the surface covering 52 relative to the thickness of the electrode 40 is not to scale. The portions 78, 80 are applied to the catheter such that the nonporous polymer portion 80 is located on the inner surface 67 thereby placing it within the blood pool, while the porous polymer portion 78 is located on the outer surface 65 thereby placing it in contact with the tissue.

The nonporous polymer portion 80 may comprise an electrically non-conductive, slippery material such as parylene or dense (non-expanded) PTFE. This nonporous polymer portion 80 serves two purposes. First, it acts as an electrical insulator to prevent alternate or non-intended site ablations, as the electrode 40 only produces a lesion through the porous polymer portion 78. Second, it allows ablation procedures to be performed using less energy since all the power to the electrode 40 is directed to the porous polymer portion 78, thus minimizing wasted power. Coagulum formation is inhibited since platelet adhesion does not occur through either the porous or nonporous polymer structure portion 78, 80.

Figure 7A:
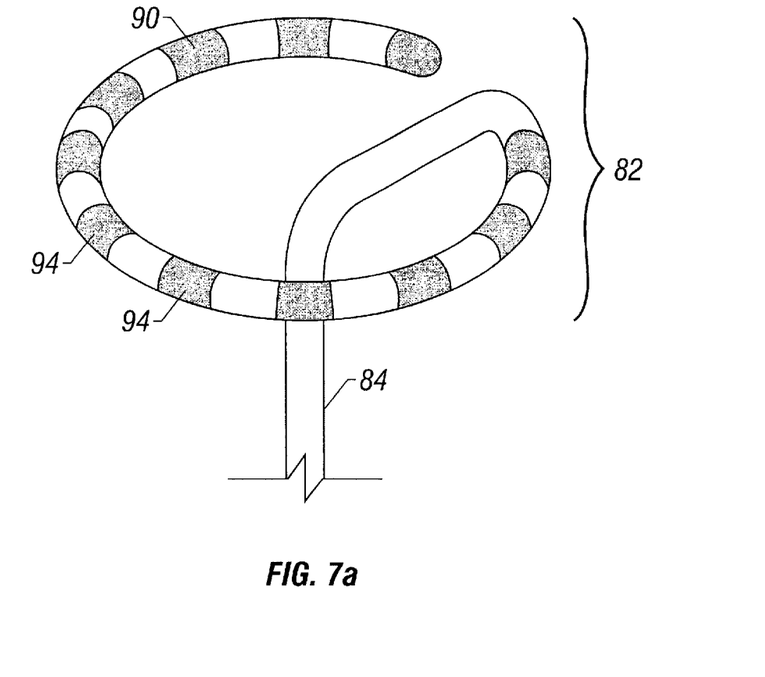
FIGS. 7a and 7b depict an alternate configuration of a catheter with a plurality of band electrodes having a surface covering.
Figure 7B:
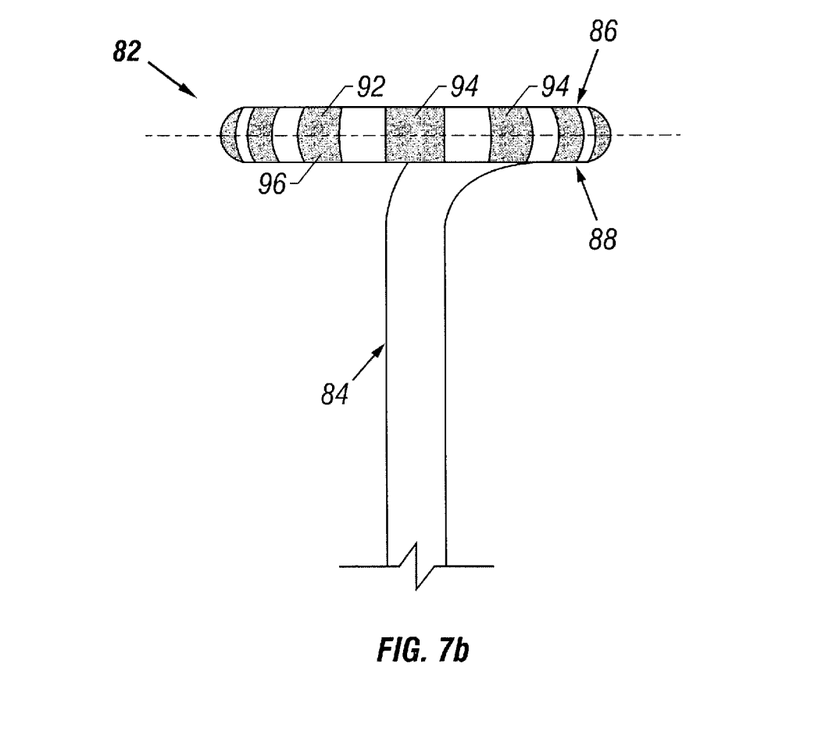

In alternate configurations of catheters employing the covered electrodes of the present invention, the distal-end region of the catheter may have a different shape then that shown in FIG. 5. For example, as shown in FIGS. 7a and 7b, the catheter may have a substantially circular shaped distal-end region 82 lying in a plane substantially perpendicular to the catheter shaft 84. In this catheter, the top-half surface 86, or front-half surface, of the distal-end region 82 defines a tissue contacting surface. A portion of the top-half surface 86 is intended to contact the biological tissue to be ablated. The bottom-half surface 88, or rear-half surface, of the distal-end region 82 defines a blood pool surface. A portion of the bottom-half surface 88 is intended to remain in the blood pool during ablation. In accordance with the present invention, a surface covering 90 having a porous polymer portion 92 and a nonporous polymer portion 96 is applied to the band electrodes 94 at the distal-end region. The nonporous polymer portion 96 is applied on the portion of the band electrodes 94 coincident with the bottom-half surface 88 thereby typically placing it within the blood pool, while the porous polymer portion 92 is applied on the portion of the band electrodes 94 coincident with the top surface 86 thereby placing it in contact with the tissue.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A catheter for applying energy to biological tissue having biological fluid flowing thereby, said catheter comprising:
    a shaft having at least one electrode;
    a layer of a bio-compatible, non-electrically conductive porous structure covering at least a portion of the surface of the electrode; and
    a layer of secondary surface covering the interior walls of the pores of the bio-compatible, non-electrically conductive porous structure.

2. The catheter of claim 1 wherein the bio-compatible, non-electrically conductive porous structure comprises a polymer structure.

3. The catheter of claim 2 wherein the porous polymer structure comprises at least one of a porous homopolymer and a porous copolymer.

4. The catheter of claim 3 wherein the porous homopolymer and the porous copolymer is based on anyone of polyurethanes, polyesters, polyolefins, polyamides, ionomers and fluoropolymers.

5. The catheter of claim 2 wherein the porous polymer structure comprises expanded polytetrafluoroethylene (ePTFE).

6. The catheter of claim 1 further comprising a layer of a metallic element covering the interior walls of the pores of the bio-compatible, non-electrically conductive porous structure.

7. The catheter of claim 6 wherein metallic element consists of one of platinum, palladium, silver, gold and platinum-10% iridium.

8. The catheter of claim 6 further comprising a layer of a wetting agent covering the metallic element.

9. The catheter of claim 1 wherein the secondary surface comprises a hydrophilic material.

10. The catheter of claim 9 wherein the hydrophilic material consists of one of polyethylene oxide, polyethylene glycol, polyvinyl alcohol, polyvinyl pyrrolidone, gelatin, polymethacrylic acid, polyhydroxyethylmethacrylate, polyacrylamide and ionic and non-ionic surfacants based on fatty acid esters.

11. The catheter of claim 1 wherein the secondary surface comprises a plasma modified material.

12. The catheter of claim 1 wherein:
the at least one electrode comprises a first surface portion and a second surface portion;
the shaft is adapted to position the electrode adjacent the biological tissue such that the first surface portion contacts the tissue and the second surface portion remains in the fluid; and
the layer of a bio-compatible, non-electrically conductive porous structure covers the first surface portion.

13. The catheter of claim 12 further comprising a layer of bio-compatible, non-electrically conductive structure covering the second surface portion.

14. The catheter of claim 13 wherein the bio-compatible, non-electrically conductive structure comprises a non-porous polymer.

15. The catheter of claim 14 wherein the non-porous polymer consists of one of polyester, polyimide, parylene, or polytetrafluoroethylene (PTFE).

16. The catheter of claim 1 wherein the biological fluid comprises blood having platelets and the size of the pores of the bio-compatible, non-electrically conductive porous structure are smaller than the size of the platelets.

17. A catheter for applying energy to biological tissue having biological fluid flowing thereby, said catheter comprising:
a shaft having a curved distal-end region with an inner surface and an outer surface;
a plurality of band electrodes positioned at the distal-end region of the shaft;
a surface covering including a first portion comprising a bio-compatible, non-electrically conductive porous structure covering a portion of each of the band electrodes; and
a secondary surface covering the interior walls of the pores of the bio-compatible, non-electrically conductive porous structure.

18. The catheter of claim 17 wherein the bio-compatible, non-electrically conductive porous structure comprises a porous polymer structure.

19. The catheter of claim 18 wherein the porous polymer structure comprises expanded polytetrafluoroethylene (ePTFE).

20. The catheter of claim 17 wherein the surface covering further covers a portion of the shaft between band electrodes.

21. The catheter of claim 17, wherein:
each of the band electrodes comprises a first surface portion that lies on the outer surface and a second surface portion that lies on the inner surface;
the shaft is adapted to position the outer surface adjacent the biological tissue and the inner surface in the fluid; and
the first portion of the surface covering covers the first surface portion of each band electrode.

22. The catheter of claim 21, wherein the surface covering further comprises a second portion comprising a bio-compatible, non-electrically conductive non-porous structure that covers the second surface portion of each band electrode.

23. The catheter of claim 22 wherein the bio-compatible, non-electrically conductive non-porous structure comprises a non-porous polymer structure.

24. The catheter of claim 23, wherein the non-porous polymer structure comprises dense (non-expanded) polytetrafluoroethylene (PTFE).

25. A catheter for applying energy to biological tissue having biological fluid flowing thereby, said catheter comprising:
a shaft having a distal-end region defining a tissue-contacting surface and a fluid-contacting surface;
a plurality of band electrodes positioned at the distal-end region of the shaft;
a surface covering including a first portion comprising a bio-compatible, non-electrically conductive porous structure that covers the portion of each of the band electrodes coincident with the tissue-contacting surface; and
a secondary surface covering the interior walls of the pores of the bio-compatible, non-electrically conductive porous structure.

26. The catheter of claim 25 wherein the bio-compatible, non-electrically conductive porous structure comprises a porous polymer structure.

27. The catheter of claim 25 wherein the surface covering further comprises a second portion comprising a bio-compatible, non-electrically conductive non-porous structure that covers the portion of each of the band electrodes coincident with the fluid-contacting surface.

28. The catheter of claim 27 wherein the bio-compatible, non-electrically conductive non-porous structure comprises a non-porous polymer structure.

* * * * *

UNITED STATES PATENT AND TRADEMARK OFFICE
CERTIFICATE OF CORRECTION

PATENT NO.    : 6,582,429 B2
DATED         : June 24, 2003
INVENTOR(S)   : Mohan Krishnan et al.

It is certified that error appears in the above-identified patent and that said Letters Patent is hereby corrected as shown below:

<u>Title page,</u>
Item [56], References Cited, U.S. PATENT DOCUMENTS, add the following:
-- 5,961,513    10/1999    Swanson et al.
   6,142,994    11/2000    Swanson et al. --.

Signed and Sealed this

Fourth Day of November, 2003

JAMES E. ROGAN
*Director of the United States Patent and Trademark Office*